United States Patent [19]
Akashi et al.

[11] Patent Number: 6,001,864
[45] Date of Patent: Dec. 14, 1999

[54] ANTIFUNGAL AGENT

[75] Inventors: Toshi Akashi; Shigeo Tanaka; Kimiko Sugita; Hideki Kohita; Michio Yamagishi; Kiyotaka Obata, all of Tokyo, Japan

[73] Assignee: Taisho Pharmaceutical Co., Ltd., Japan

[21] Appl. No.: 08/952,433

[22] PCT Filed: Jun. 7, 1996

[86] PCT No.: PCT/JP96/01553

§ 371 Date: Nov. 20, 1997

§ 102(e) Date: Nov. 20, 1997

[87] PCT Pub. No.: WO96/40121

PCT Pub. Date: Dec. 19, 1996

[30] Foreign Application Priority Data

Jun. 7, 1995 [JP] Japan .................................. 7-140598

[51] Int. Cl.⁶ ........................ A61K 31/415; A61K 31/14
[52] U.S. Cl. ........................ 514/399; 514/642; 514/643
[58] Field of Search ................... 514/399, 642, 514/643

[56] References Cited

U.S. PATENT DOCUMENTS

| 5,143,917 | 9/1992 | Paradies | 514/256 |
|---|---|---|---|
| 5,335,373 | 8/1994 | Dangman et al. | 2/161.7 |
| 5,661,170 | 8/1997 | Chodosh | 514/390 |

FOREIGN PATENT DOCUMENTS 0094167  11/1983  European Pat. Off. .

OTHER PUBLICATIONS

XP–002069331, Database Medline, Abstract, Pavlenko, SA, Vestnik OtorinolaringologII, Jul.–Aug., 1990 vol. 4, 1990, pp. 70–74.
Patent Abstracts of Japan, vol. 017, No. 704, Dec. 22, 1993, (c–1146) Teisan Seiyaku KK.
XP–002069332, Database WPI, Week 9033, Derwent Pub. CN 1036902 (Microbe Epidemic DI), Huang, J. (1986).
XP–002069333, Database WPI, Week 9046, Derwent Pub. Oct. 8, 1990, Abstract, JP 02 250 833, Yamaguchi Yakuhin KK.
Patent Abstacts of Japan, vol. 011, No. 008 (c–396) Jan. 9, 1987, & JP 61 186 318 A, Yougo Takaoka, Aug. 20, 1986.
Anmo et al–Yakuzaigaku, 26(3) 189–92 Japan (Abstract) 1966.
Lio–Po et al–J. Fish Dis, 5(2), 97–112 (abstract), 1982.

*Primary Examiner*—Raymond Henley, III
*Attorney, Agent, or Firm*—Lorusso & Loud

[57] ABSTRACT

An antifungal composition including an imidazole-type antifungal compound and a quaternary ammonium salt is a medicament having a far more potentiated activity of miconazole nitrate and a higher therapeutic effect, and is effective against both Trichophyton and Candida.

3 Claims, 6 Drawing Sheets

FIG. 6

ANTIFUNGAL AGENT

This is a 371 of PCT/JP96/01553 filed Jun. 7, 1996.

TECHNICAL FIELD

This invention relates to an antifungal composition. More particularly, it is concerned with an antifungal composition wherein an imidazole-type antifungal compound is combined with a quaternary ammonium salt.

BACKGROUND ART

Imidazole-type antifungal compounds, as worldwide, leading antifungal agents, are those having an imidazole group in the chemical structure thereof. They have been believed to exhibit an antifungal activity mainly by damaging the cell membrane of fungi.

For those imidazole-type antifungal agents, there have been suggested as an active ingredient for OTC drugs clotrimazole, miconazole nitrate, econazole nitrate, bifonazole, oxiconazole nitrate, sulconazole nitrate, tioconazole and the like.

Clotrimazole has been applied as external preparations solely and is effective against Trichophyton and also Candida. If applied to the healthy skin, in vivo absorption of the agent can hardly be observed, while local side-effects such as irritating feeling, flare, anthema and the like in the skin are believed to be manifested as a direct irritating effect on the skin or allergic effect.

Bifonazole exhibits a similar action to that of clotrimazole and is effective for many human pathogenic fungi. It is said that this agent possesses a more excellent skin permeability in external use and a higher drug retention in the cutaneous tissues as compared with other imidazole-type antifungal agents. As is similarly seen with clotrimazole, local side-effects such as irritating feeling, flare, anthema and the like in the skin are manifested.

Miconazole nitrate and econazole nitrate exert an antifungal activity against Trichophyton, Candida, Aspergillus, Cryptococcus and others. When applied to the healthy skin, in vivo absorption of these agents can hardly be observed, while similar local side-effects to those of clotrimazole are observed and a very few systemic side-effects are observed, when applied externally in a conventional manner.

The term a quaternary ammonium salt as used herein refers to a cationic surfactant which is a quaternary ammonium salt. It may include benzethonium chloride, benzalkonium chloride, dequalinium chloride and the like. It has been supposed that the cation released from the quaternary ammonium salt might be adsorbed on the microbial surface and then carried into the cells to affect the cellular proteins, whereby an antifungal activity could be exerted.

Benzethonium chloride and benzalkonium chloride exert an antimicrobial activity against gram bacteria and fungi, while it is known that long term application of these agents to the skin brings about side-effects of hypersensitiveness such as chapped skin, flare, itching and others.

Dequalinium chloride has been reported to exert an antimicrobial activity against bacteria (especially, Staphylococcus aureus and hemolytic streptococci) and fungi. It has been dispensed mainly for buccal antifungal agents or antiodontalgic and antipyorrheal agents.

Although there has not yet been reported a medicament wherein an imidazole-type antifungal compound is blended or combined with a quaternary ammonium salt, U.K. Patent No. 2 208 598A discloses a combination of an imidazole-type antifungal compound with salicylic acid or benzoic acid.

DISCLOSURE OF INVENTION

Treatment of athlete's foot, radical cure of which is generally said to be difficult, requires continuous application of a medicament over a prolonged period of time. The symptom of athlete's foot appears suppressed in the winter season, but this never means complete cure of the disease but simply a slowdown of the fungal activity. Thus, there has been desired a development of a medicament having a higher therapeutic effect. Moreover, it is difficult to discriminate whether phathogenesis of athlete's foot may be caused by Trichophyton or Candida, and it can be done only by means of a microscopic examination by a medical specialist or the cultivation of the pathogenic microbe. Therefore, a medicament which is effective against both of those pathogenic fungi is important. Furthermore, the imidazole-type antifungal compounds may show, as mentioned above, local side-effects such as irritating feeling, flare, anthema and the like in the skin. Therefore a need exists to eliminate side-effects by reducing the amount of said compound to be blended.

We have conducted various screenings in order to select an agent capable of effectively acting together with the imidazole-type antifungal compound and having an antifungal activity against both Trichophyton and Candida and in order to improve the feeling in use thereof. Now, we have found that a certain quaternary ammonium salt has a synergistically potentiating effect on an antifungal activity, on the basis of which this invention has been completed.

More specifically, this invention is directed to an antifungal composition which comprises an imidazole-type antifungal compound in combination with a quaternary ammonium salt.

Of the imidazole-type antifungal compounds, miconazole, econazole, clotrimazole, bifonazole and the like are preferable. Miconazole and econazole may be employed also in the form of salts thereof. In particular, nitrates thereof have been widely employed.

The quaternary ammonium salt as used herein is a cationic surfactant in the form of a quaternary ammonium salt. In this invention, there may be preferably employed benzethonium chloride, benzalkonium chloride, dequalinium chloride and the like.

The amount of the imidazole-type antifungal compound to be blended is 0.2–1% by weight, preferably 0.5–1% by weight.

The amount of the quaternary ammonium salt to be blended is 0.1–1% by weight, preferably 0.5–1% by weight. For example, the amount of benzethonium chloride to be blended is 0.5–1.0% by weight, while the amount of benzalkonium chloride to be blended is 0.1–1% by weight, preferably 0.5–1% by weight.

The quaternary ammonium salt is preferably blended at 0.1–1 part by weight, more preferably 0.1–0.5 part by weight, per 1 part by weight of the imidazole-type antifungal compound.

The active ingredient of this invention may be formulated as external preparations such as solutions, lotions, emulsions, tinctures, ointments, creams, aqueous gels, oily gels, aerosols and the like, by blending known additives, if necessary, according to a conventional method.

For aqueous components, there may be mentioned propylene glycol, 1,3-butylene glycol, glycerol, ethanol, macrogols and the like.

For oily components, there may be mentioned diisopropyl adipate, stearyl alcohol, cetyl alcohol, squalene, medium chain fatty acid triglycerides and the like.

As polymers, there may be mentioned a carboxyvinyl polymer, methyl cellulose and the like.

As pH adjustors, there may be mentioned citric acid, inorganic bases such as sodium hydroxide and the like, organic amines such as diisopropanolamine and the like, and others.

As antioxidants, there may be mentioned dibutyl hydroxytoluene (BHT), butyl hydroxyanisole (BHA), α-tocopherol, erythorbic acid, sodium pyrosulfite and the like.

As coloring agents, there may be mentioned titanium oxide and the like.

As surfactants, there may be mentioned polyoxyethylene hardened castor oil, sorbitan monostearate, sorbitan monopalmitate, monostearic acid glycerides, sorbitan monolaurate, polyoxyethylene-polyoxypropylene block copolymer, polysorbates, sodium lauryl sulfate, sucrose fatty acid esters, lecithin and the like.

As stabilizers, there may be mentioned EDTA-2Na and the like.

A particularly preferred embodiment of this invention is directed to an antifungal composition which comprises an imidazole-type antifungal compound in combination with dequalinium chloride.

More specifically, those quaternary ammonium salts, the synergistic antifungal effect of which had been established, were further examined with regard to their skin irritation, their formulation into pharmaceutical preparations and others, and, as a result, it has been found that dequalinium chloride is most preferred as shown in Table 1.

TABLE 1

| Name of compound | Adaptability as pharmaceutical preparation | Skin irritating property |
| --- | --- | --- |
| Benzalkonium chloride | ○ | Δ |
| Dequalinium chloride | ○ | ○ |

In the present invention, an effective amount of miconazole nitrate to be blended is 0.2–1% by weight, preferably 0.5–1% by weight.

An effective amount of dequalinium chloride to be blended is 0.05–0.5% by weight, preferably 0.1–0.5% by weight.

Dequalinium chloride is used at 0.1–1 part by weight, preferably 0.1–0.5 part by weight, per 1 part by weight of miconazole nitrate.

INDUSTRIAL APPLICABILITY

The pharmaceutical composition of this invention is a very potent antifungal agent with a potentiated antifungal activity.

The effect of this invention will be illustrated by the following examples.

TEST EXAMPLE 1

(1) Test strains

The following microorganisms were used as test strains:

Trichophyton rubrum

Trichophyton mentagrophytes (2) Preparation of spore suspension

The test strain was inoculated onto a slant in a test tube containing ⅒ Sabouraud's agar medium and cultivation was conducted at 28° C. for 3–4 weeks. After completion of the cultivation, the mycelia were collected by scratching with a sterile spatula and transferred into an Erlenmeyer flask (100 ml volume) containing sterilized glass beads and 10 ml of physiological saline containing 0.1% Tween 80 and then shaken for one hour. Then, the mixture was filtered through a cotton plug to give a spore suspension. The spore suspension was stored under refrigeration and used within one month.

(Composition of ⅒ Sabouraud's agar medium)

Glucose 4.0 g, peptone 1.0 g, potassium dihydrogenphosphate (anhydrous) 1.5 g, magnesium sulfate (heptahydrate) 1.0 g, sodium nitrate 1.0 g, agar 20.0 g, distilled water 1000 ml (3) Preparation of test compositions Test compositions were prepared by using miconazole nitrate and benzalkonium chloride, dequalinium chloride, benzethonium chloride or salicylic acid, dissolving them and then preparing doubling dilutions with DMSO as a dilution solvent so as to correspond to the test concentrations.

(4) Test procedure

The diluted composition and Sabouraud's agar medium (Eiken Chemical Co., Ltd.) were admixed at a ratio of 1:99 and solidified and then the spore suspension was inoculated at about $10^5$ spores/ml. Cultivation was conducted at 28° C. for 5 days and any growth of the fungus was confirmed.

The DMSO concentration was maintained at 1% or less so as not to affect the spore germination.

(5) Evaluation and calculation equation

Evaluation of a synergistic effect was made by calculating FIC index (Fractional Inhibitory Concentration index) from the minimum concentration of the composition (MIC: The minimum inhibitory concentration, μg/ml), at which no growth of a microorganism was observed at the end of the cultivation.

$$\text{FIC index} = a/a_0 + b/b_0 \quad \text{(Calculation equation)}$$

a: MIC of miconazole nitrate when used together with the test agent $a_0$: MIC of miconazole nitrate alone b: MIC of the test agent when used together with miconazole nitrate $b_0$: MIC of the test agent alone (Evaluation) Combined effect of the test agents was evaluated according to the following ratings:

>2: Antagonism

Not more than 2 —more than 1: Addition

Not more than 1: Synergism (6) Results

The rating of not more than 1.0 was defined to demonstrate the development of synergism, taking into consideration the facts that the FIC index value for determining any synergism is to evaluate a bacteriostatic action and that this test is a primary screening. As a result, almost all test agents were established to show an additive or synergistic effect as shown in Table 2.

TABLE 2

| | FIC index | |
| --- | --- | --- |
| Name of compound | T. rubrum | T. mentagrophytes |
| Benzethonium chloride | 0.49 | 0.55 |
| Benzalkonium chloride | 0.12 | 0.26 |

TABLE 2-continued

| | FIC index | |
|---|---|---|
| Name of compound | T. rubrum | T. mentagrophytes |
| Dequalinium chloride | 0.47 | 0.68 |
| Salicylic acid | 0.44 | 0.72 |

TEST EXAMPLE 2

(1) Test strains

The following microorganisms were used as test strains:
Trichophyton rubrum
Trichophyton mentagrophytes (2) Preparation of spore suspension It was prepared in the same manner as described in Test Example 1.

(3) Preparation of test compositions

Test compositions were prepared by using miconazole nitrate, econazole nitrate, clotrimazole or bifonazole and dequalinium chloride, dissolving them and then preparing doubling dilutions with DMSO as a dilution solvent so as to correspond to the test concentrations.

(4) Test procedure

It was carried out in the same manner as described in Test Example 1.

(5) Evaluation and calculation equation

Calculation and evaluation were performed in the same manner as described in Test Example 1.

(6) Results

The results are shown in Table 3.

TABLE 3

Synergistic effect of imidazole-type antifungal compounds and dequalinium chloride

| | FIC index | |
|---|---|---|
| Name of compound | T. rubrum | T. mentagrophytes |
| Miconazole nitrate | 0.32 | 0.53 |
| Econazole nitrate | 0.63 | 1.00 |
| Clotrimazole | 0.38 | 1.25 |
| Bifonazole | 0.25 | 0.14 |

As a result, the test compositions showed a potent synergistic effect with dequalinium chloride, except for the effect of clotrimazole on T. mentagrophytes as shown in Table 3.

The above results reveal that the synergistic effect by a combination with dequalinium chloride can be developed not only in case of miconazole nitrate but also the whole imidazole-type antifungal compounds.

TEST EXAMPLE 3

(1) Test strains

The following microorganisms were used as test strains:
*Trichophyton rubrum*
*Trichophyton mentagrophytes*

(2) Preparation of spore suspension

It was prepared in the same manner as described in Test Example 1.

(3) Preparation of test compositions

Test compositions were prepared by using miconazole nitrate (MCZ) and salicylic acid, benzalkonium chloride (BAC) or dequalinium chloride (DQ), dissolving and then preparing doubling dilutions with DMSO as a dilution solvent so as to correspond to the test concentrations.

(4) Test procedure

To 20 ml of 20 mM phosphate buffer (pH 6.5) sterilized by filtration was added and admixed 100 μl each of the test compositions and then the spore suspension was added so as to be $10^5$ spores/ml (usually 50–200 μl) followed by stirring. While incubated at 30° C., the number of surviving spores was measured on day 0, 1, 2 and 3 after testing, respectively.

In this connection, the DMSO concentration was maintained at 1% or less so as not to affect the spore germination.

(5) Measurement of number of surviving spores

The number of surviving spores in the spore suspension and the test solution was measured by preparing 10 times dilutions using sterile physiological saline or LP dilution liquid (DAIGO), smearing 50 μl each of the diluted liquids onto the Sabouraud's agar medium (Eiken Chemical Co., Ltd.) previously prepared, cultivating the medium at 28° C. for 4 days or more in the case of *T. rubrum* or for 3 days or more in case of *T. mentagrophytes,* and then calculating the number of surviving spores in the spore suspension or the test solution from the number of the colonies as grown.

(6) Evaluation of synergism

In accordance with the literature (Antimicrobial Agents and Chemotherapy, Feb. 1977, pp. 225–228), the test compositions were evaluated as synergistic, if the difference between the number of surviving spores when used alone and that of surviving spores when used in combination is of about 2 or more orders.

[Test results]

(1) Fungicidal activity curve of miconazole nitrate

Figure 1:
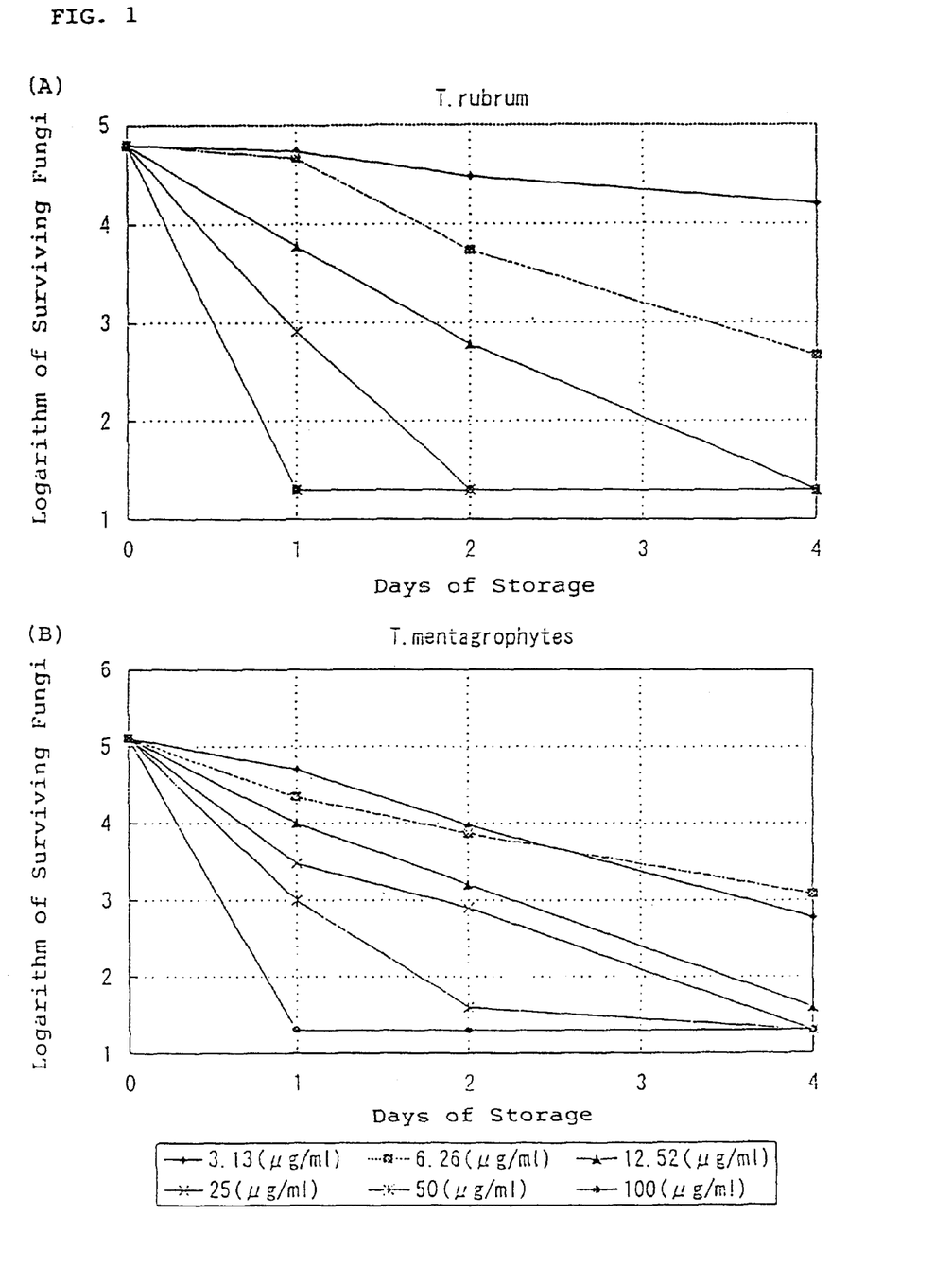
FIG. 1 graphically shows the fungicidal activity of miconazole nitrate against *T. rubrum* (A) and *T. mentagrophytes* (B). The number of storage days is plotted on the abscissa and a logarithm of the number of surviving fungi/ml is on the ordinate (That is, 1 means $10^1$ spores/ml, 2 does $10^2$ spores/ml, 3 does $10^3$ spores/ml and 4 does $10^4$ spores/ml).

The fungicidal activity of miconazole nitrate alone was determined in sterile physiological saline (pH 6.5). As a result, the fungicidal activity was potentiated in a concentration-dependent manner as shown in FIG. 1. The test for the combined effect was made at a selected concentration of 3.13 μg/ml, at which a synergistic fungicidal activity can be easily evaluated.

(2) Fungicidal activity curve when used together with agents

The maximum blending ratios within the criterion of each agent to miconazole nitrate are shown in Table 4.

TABLE 4

| Name of compound | Blending ratio* |
|---|---|
| Salicylic acid | 10 |
| Benzalkonium chloride | 1 |
| Degualinium chloride | 0.5 |

*when an amount of the miconazole nitrate to be blended is defined as 1

The fungicidal activity when used in combination was confirmed by adding each agent at the maximum blending ratio to 3.13 μg/ml of miconazole nitrate.

Figure 2:
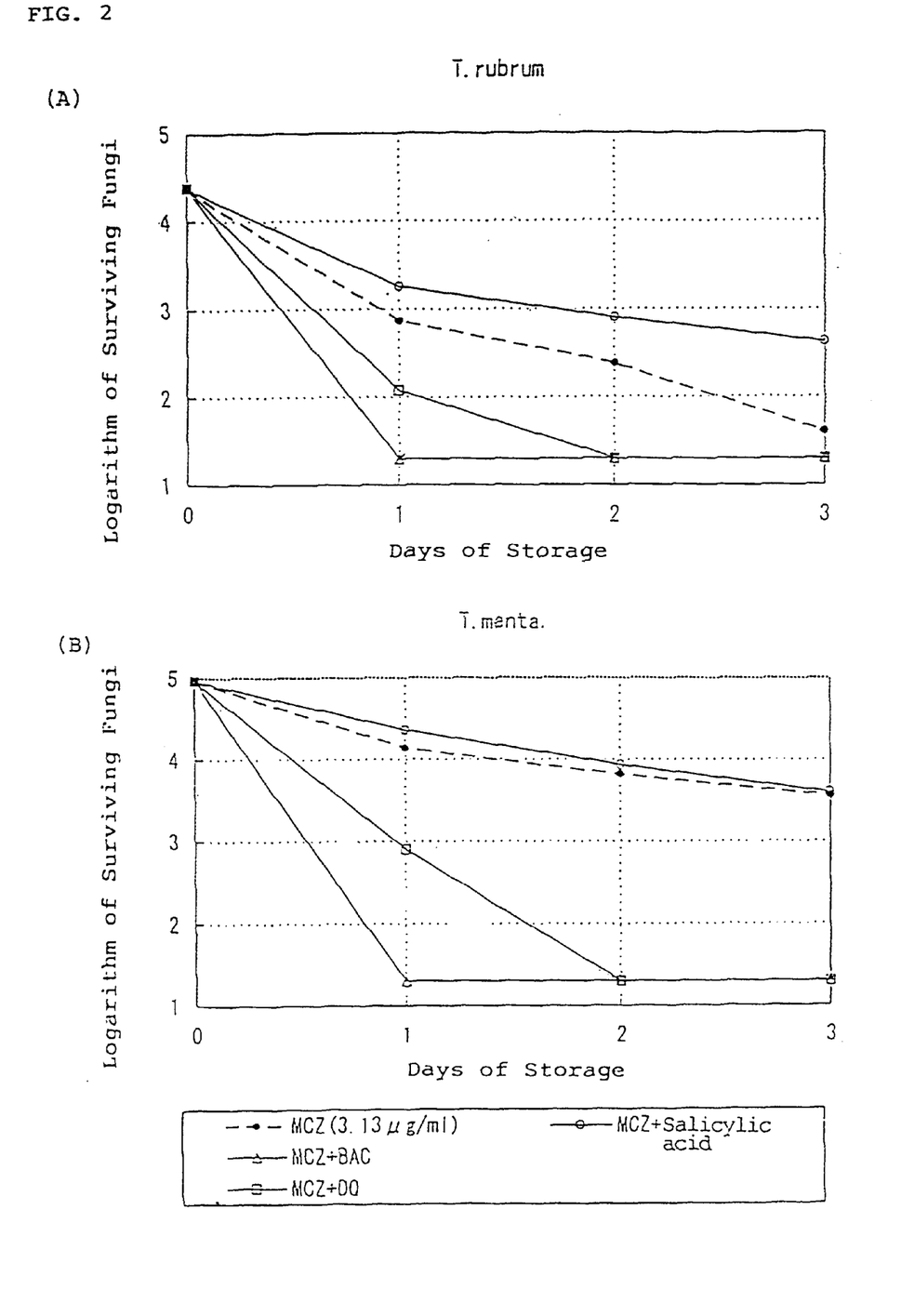
FIG. 2 graphically shows the fungicidal activity of a combination of the antifungal compound with the agent against *T. rubrum* (A) and *T. mentagrophytes* (B). The number of storage days is plotted on the abscissa and a logarithm of the number of surviving fungi/ml is on the ordinate. MCZ represents mioconazole nitrate, BAC represents benzalkonium chloride and DQ does dequalinium chloride.

As shown in FIG. 2, it has been confirmed that the fungicidal activity when used in combination was much more potentiated than that of miconazole alone, except for the case of salicylic acid.

Figure 3:
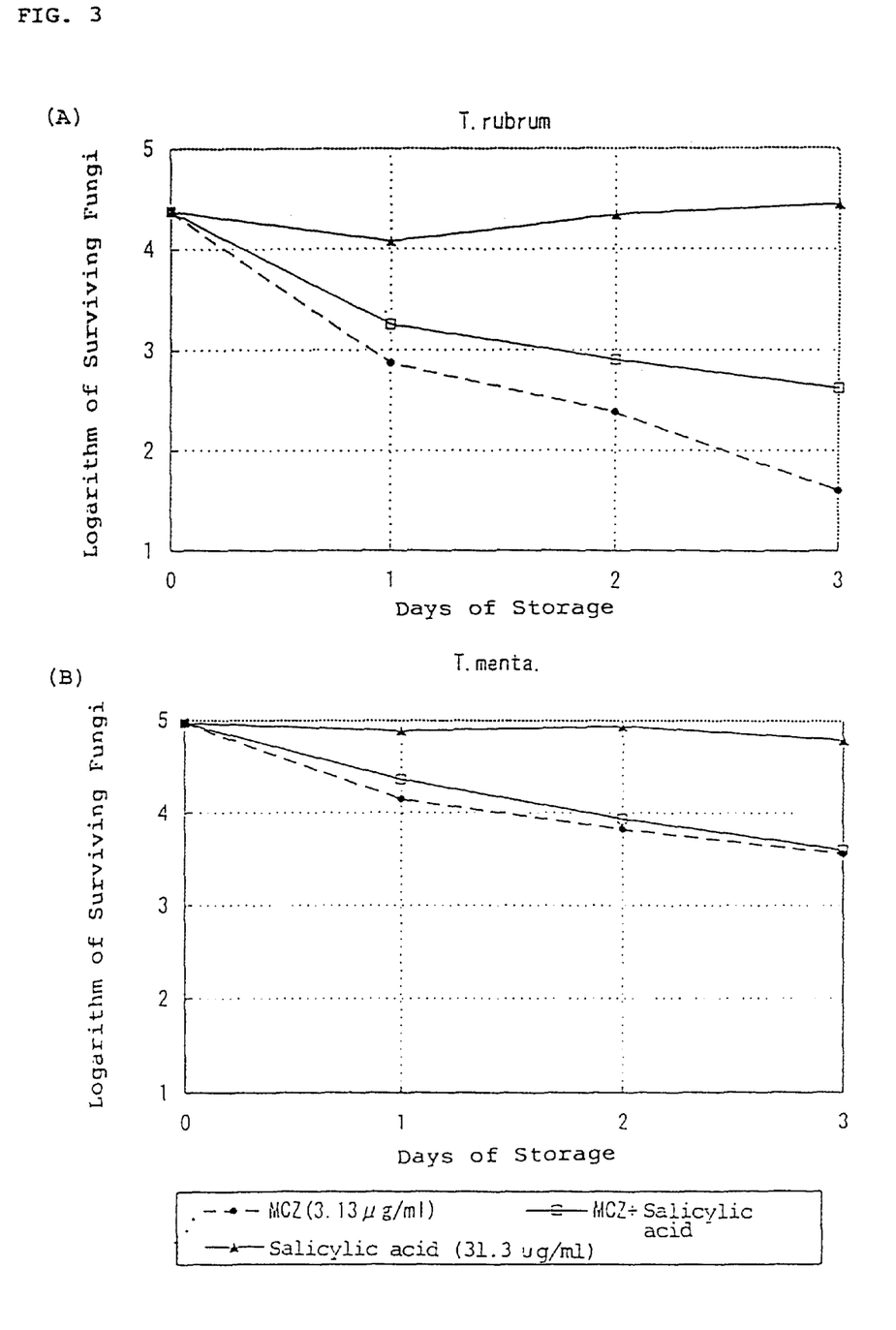
FIG. 3 graphically shows the fungicidal activity of the antifungal compound used together with salicylic acid against *T. rubrum* (A) and *T. mentagrophytes* (B). The number of storage days is plotted on the abscissa and a logarithm of the number of surviving fungi/ml is on the ordinate. MCZ represents miconazole nitrate.

The effect of each agent was studied in detail as follows:

The effect by salicylic acid is illustrated in FIG. 3.

No fungicidal activity was observed when salicylic acid was used alone, while the fungicidal activity in combined use was equal to or less than that of miconazole nitrate alone. In view of the results of the FIC index from the primary screening, it is also assumed that the combined effect of salicylic acid may be of a bacteriostatic one.

Figure 4:
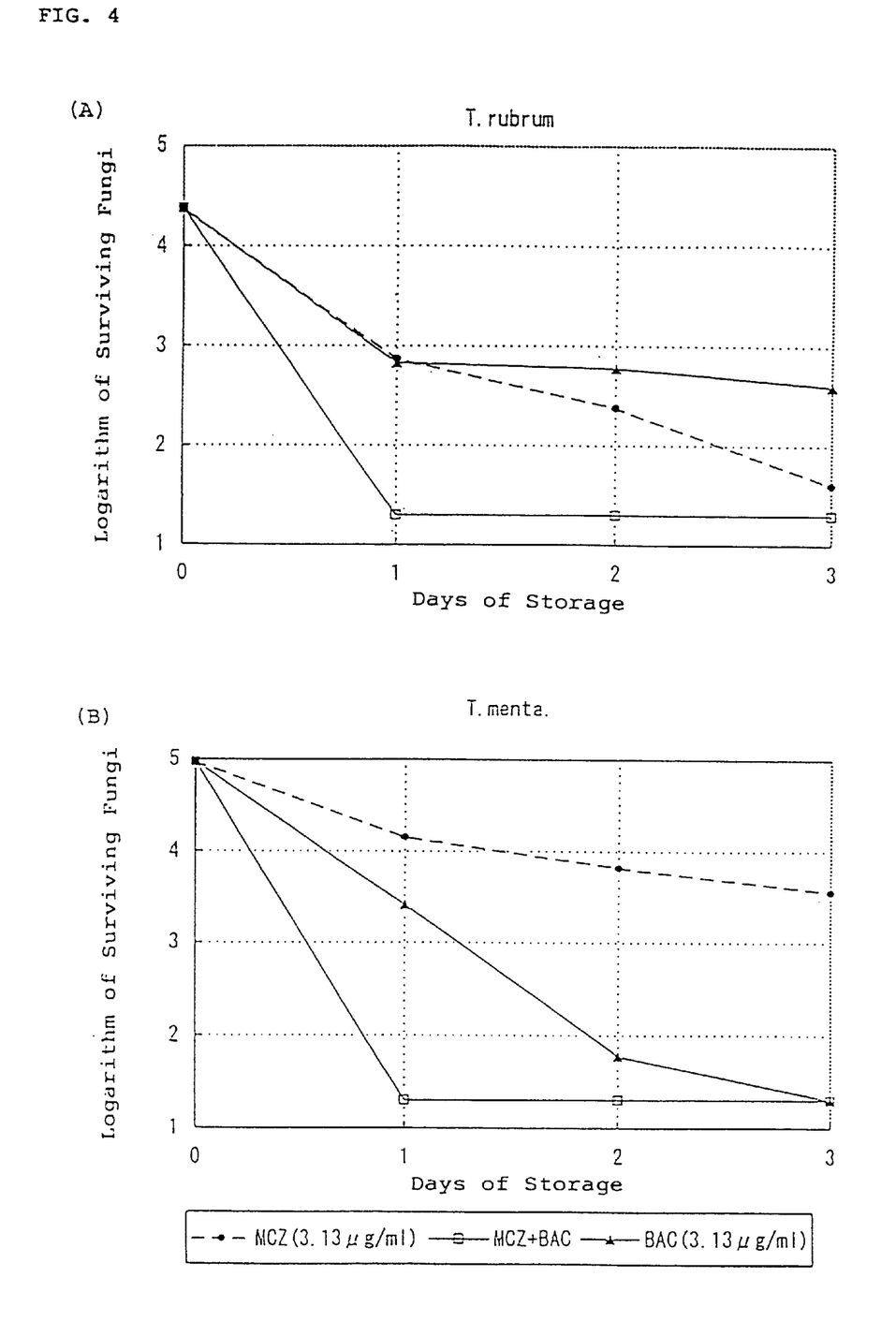
FIG. 4 graphically shows the fungicidal activity of the antifungal compound used together with benzalkonium chloride against *T. rubrum* (A) and *T. mentagrophytes* (B). The number of storage days is plotted on the abscissa and a logarithm of the number of surviving fungi/ml is on the ordinate. MCZ represents miconazole nitrate and DQ represents dequalinium chloride.

The effect by benzalkonium chloride is illustrated in FIG. 4.

When benzalkonium chloride was used alone, the fungicidal activity was of the same level as miconazole nitrate in case of T. rub. or of the higher level than that of miconazole nitrate in case of T. menta., while the fungicidal activity in the combined use was less than the detection limit in both fungi on day 1.

Figure 5:
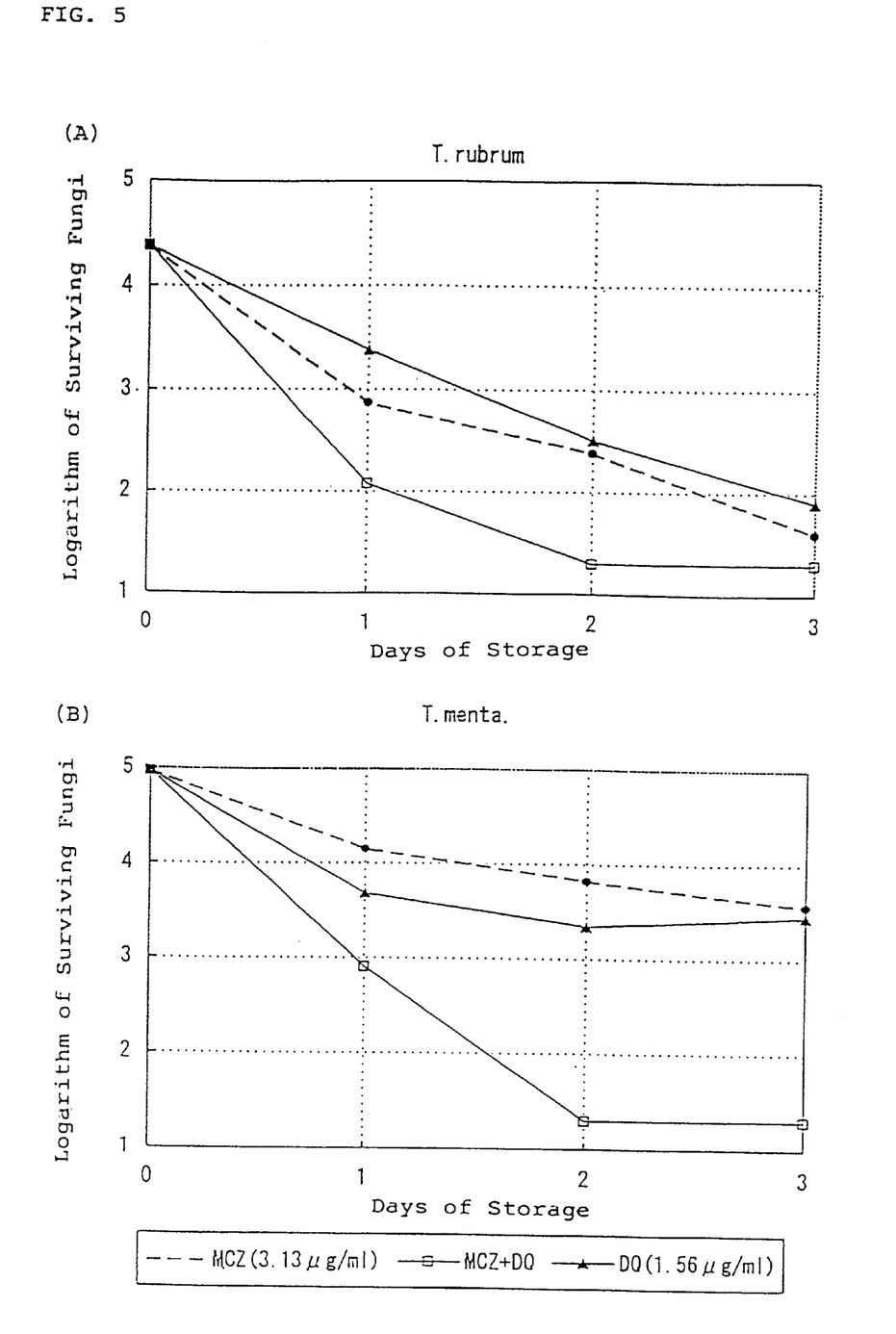
FIG. 5 graphically shows the fungicidal activity of the antifungal compound used together with dequalinium chloride against *T. rubrum* (A) and *T. mentagrophytes* (B). The number of storage days is plotted on the abscissa and a logarithm of the number of surviving fungi/ml is on the ordinate. MCZ represents miconazole nitrate and DQ represents dequalinium chloride.

The effect by dequalinium chloride is illustrated in FIG. 5.

The fungicidal activity of dequalinium chloride alone was equal to that of miconazole nitrate alone and was less than the detection limit when used in combination on day 2.

In accordance with the literature (Antimicrobial Agents and Chemotherapy, Feb. 1977, pp. 225–228), synergism in fungicidal activity is evaluated effective if a difference in the number of surviving spores is of 2 or more orders between the single use and the combined use. Therefore, benzalkonium chloride and dequalinium chloride have been evaluated to exert a synergistic fungicidal activity.

TEST EXAMPLE 4

(1) Test strains

The following microorganisms were used as test strains:
Candida albicans
Staphylococcus aureus (2) Preparation of microbial suspension Candida albicans was cultivated on Sabouraud's agar medium (Eiken Chemical Co., Ltd.) at 28° C. for 24 hours and then suspended in sterile physiological saline so as to form a microbial suspension of about $10^6$/ml.

Staphylococcus aureus was cultivated on Mueller-Hinton agar medium (Eiken Chemical Co., Ltd.) at 37° C. for 18 hours and then suspended in sterile physiological saline so as to form a microbial suspension of about $10^6$/ml.

(3) Preparation of test compositions

Test compositions were prepared by using miconazole nitrate and dequalinium chloride, dissolving them and then preparing doubling dilutions with DMSO as a dilution solvent so as to correspond to the test concentrations.

(4) Test procedure

The diluted composition and Sabouraud's agar medium (Eiken Chemical Co., Ltd.) were admixed at a ratio of 1:99 and solidified and then the microbial suspension of Candida albicans was inoculated. Cultivation was conducted at 30° C. for 2 days and any growth of the fungus was confirmed.

The diluted composition and Mueller-Hinton agar medium (Eiken Chemical Co., Ltd.) were admixed at a ratio of 1:99 and solidified and then the microbial suspension of Staphylococcus aureus was inoculated. Cultivation was conducted at 30° C. for 24 hours and any growth of the bacterium was confirmed.

(5) Evaluation and calculation equation

Calculation and evaluation were performed in the same manner as described in Test Example 1.

(6) Results

The results are shown in Table 5.

TABLE 5

| Test strain | FIC index |
| --- | --- |
| Candida albicans | 0.11 |
| Staphylococcus aureus | 0.75 |

Synergism by a combination of miconazole nitrate with dequalinium chloride)was also observed against Candida albicans and Staphylococcus aureus.

TEST EXAMPLE 5

Figure 6:
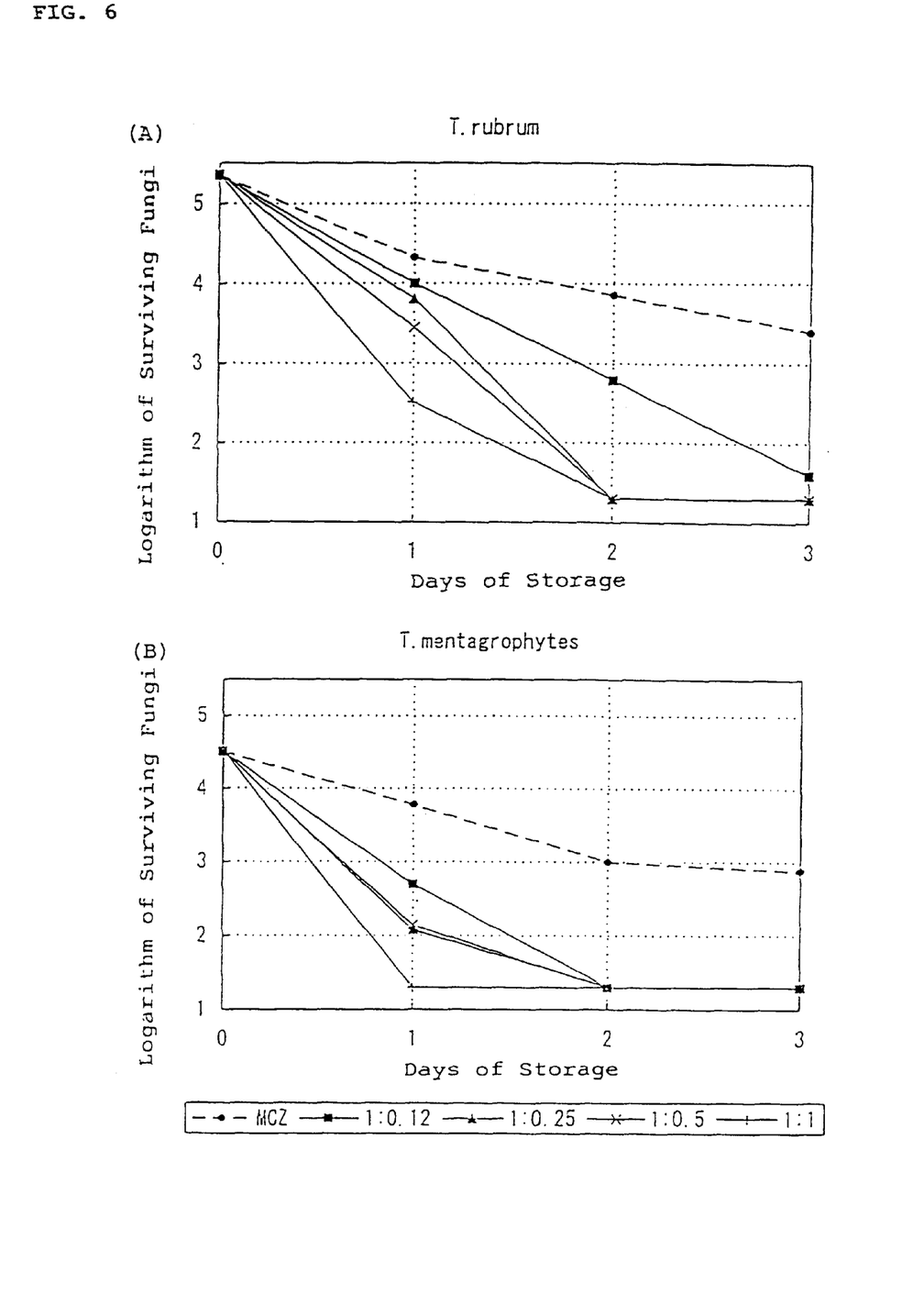
FIG. 6 graphically shows the results from studies on influence upon the blending ratio of miconazole nitrate with dequalinium chloride. The number of storage days is plotted on the abscissa and a logarithm of the number of surviving fungi/ml is on the ordinate. MCZ represents miconazole nitrate.

Influence of the blending ratio (1:0.12–1.00) of miconazole nitrate and dequalinium chloride was studied following the same test procedure as described in Test Example 3 and the results are shown in FIG. 6.

As a result, it was found that a blending ratio of 1:0.12 or more gave a much more potent fungicidal activity than that of miconazole nitrate alone or dequalinium chloride alone and synergism was also observed.

TEST EXAMPLE 6

Influence of lecithin

Lecithin, which has been employed as a base for creams, is known to be an inactivating agent for fungicides such as quaternary ammonium salts and the like [Tadaichi ISH-IZEKI et al., the Journal of the National Institute of Hygienic Sciences, No. 91 (1973)], and its influence on synergism of miconazole nitrate with dequalinium chloride was studied.

The same test procedure as described in Test Example 3 was repeated with a lecithin concentration which was adjusted to a blending ratio (miconazole nitrate:lecithin= 1:0.5) in case of miconazole nitrate alone, or with a lecithin concentration of 1.57 μg/ml when dequalinium chloride was used alone or in combination with miconazole nitrate.

As a result, no influence was observed at these concentrations.

BEST MODE FOR CARRYING OUT THE INVENTION

This invention will be explained in detail by the following examples.

EXAMPLE 1

(Example of Formulation for Creams)

| | |
| --- | --- |
| Miconazole nitrate | 100 g |
| Lidocaine | 200 g |
| Dequalinium chloride | 10 g |
| Polyoxyethylene sorbitan monostearate | 400 g |
| Sorbitan monostearate | 200 g |
| 1,3-Butylene glycol | 1,500 g |
| Medium chain fatty acid triglyceride | 1,500 g |
| Glycerol monostearate | 250 g |
| EDTA-2Na | 10 g |
| Purified water | q.s. to a total of 10,000 g |

(Preparation)

To aqueous phase components (1,3-butylene glycol, EDTA-2Na, dequalinium chloride and purified water) were added oily phase components (miconazole nitrate, lidocaine, sorbitan monostearate, medium chain fatty acid triglyceride, glycerol monostearate and polyoxyethylene sorbitan monostearate), and the mixture was warmed to prepare 10,000 g of creams.

EXAMPLE 2

(Example of Formulation for Solutions)

| | |
| --- | --- |
| Miconazole nitrate | 100 g |
| Dequalinium chloride | 20 g |
| Dipotassium glycyrrhizinate | 50 g |
| BHT | 5 g |
| Ethanol | 5,000 g |
| Purified water | q.s. to a total of 10,000 ml |

(Preparation)

In the ethanol were dissolved the other agents and the purified water was added to make up a total volume to 10,000 ml.

EXAMPLE 3
(Example of Formulation for Gel Creams)

| | |
|---|---|
| Miconazole nitrate | 100 g |
| Dequalinium chloride | 20 g |
| Lidocaine | 200 g |
| Polyoxyethylene sorbitan monostearate | 100 g |
| Propylene glycol | 1,000 g |
| Liquid paraffin | 500 g |
| Stearyl alcohol | 100 g |
| Carboxyvinyl polymer | 50 g |
| Diisopropanolamine | 100 g |
| Purified water | q.s. to a total of 10,000 g |

(Preparation)

Oily phase components (the miconazole nitrate, lidocaine, dequalinium chloride, polyoxyethylene sorbitan monostearate, liquid paraffin and stearyl alcohol) were dissolved by warming and allowed to cool to room temperature. Then, the carboxyvinyl polymer was dissolved in the water and the propylene glycol and allowed to stand at room temperature to make the carboxyvinyl polymer swollen. The said oily phase and aqueous phase were stirred at room temperature to prepare gel creams.

EXAMPLE 4
(Example of Formulation for Aerosols)
Concentrate:

| | |
|---|---|
| Miconazole nitrate | 50 g |
| Degualinium chloride | 5 g |
| Dipotassium glycyrrhizinate | 25 g |
| Ethanol | 2,500 g |
| Purified water | 5,000 ml |
| Propellant: | 5,000 ml |
| LPG | |

(Preparation)

Main active ingredients were dissolved in a base composed of the ethanol and the water to form a stock solution, which was then charged into a container. A valve was fitted with the container, into which the propellant was then injected to prepare aerosols.

We claim:

1. A synergistic antifungal composition which comprises miconazole nitrate and dequalinium chloride.

2. The antifungal composition according to claim 1 comprising 0.1 to 1 part by weight of said dequalinium chloride to 1 part by weight of said miconazole nitrate.

3. The antifungal composition according to claim 2 wherein said miconazole nitrate is 0.2–1.0 wt. % of the composition.

* * * * *